(12) United States Patent
Hatsuyama et al.

(10) Patent No.: US 8,168,429 B2
(45) Date of Patent: May 1, 2012

(54) METHOD OF AMPLIFYING HEMATOPOIETIC STEM CELL AND HEMATOPOIETIC PROGENITOR CELL

(75) Inventors: Asako Hatsuyama, Kobe (JP); Kiminari Ito, Kobe (JP); Tatsutoshi Nakahata, Kyoto (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 0 days.

(21) Appl. No.: 10/587,014

(22) PCT Filed: Jul. 21, 2004

(86) PCT No.: PCT/JP2004/010677
§ 371 (c)(1),
(2), (4) Date: Dec. 5, 2006

(87) PCT Pub. No.: WO2005/071064
PCT Pub. Date: Aug. 4, 2005

(65) Prior Publication Data
US 2007/0166825 A1    Jul. 19, 2007

(30) Foreign Application Priority Data

Jan. 21, 2004 (JP) ................................ 2004-013291

(51) Int. Cl.
*C12N 5/071* (2010.01)
*C07K 14/475* (2006.01)
*C07K 14/54* (2006.01)
*C07K 14/76* (2006.01)

(52) U.S. Cl. ........ 435/377; 435/325; 435/384; 435/386; 435/388; 530/350; 530/362; 530/399

(58) Field of Classification Search .................... None
See application file for complete search history.

(56) References Cited

U.S. PATENT DOCUMENTS

| | | | |
|---|---|---|---|
| 5,405,772 A * | 4/1995 | Ponting | 435/378 |
| 5,635,386 A * | 6/1997 | Palsson et al. | 435/372 |
| 5,646,043 A * | 7/1997 | Emerson et al. | 435/373 |
| 5,945,337 A | 8/1999 | Brown | |
| 6,037,174 A | 3/2000 | Smith et al. | |
| 6,224,860 B1 | 5/2001 | Brown | |
| 6,372,210 B2 | 4/2002 | Brown | |
| 6,383,480 B1 | 5/2002 | Kikuchi et al. | |
| 6,733,746 B2 * | 5/2004 | Daley et al. | 424/93.21 |
| 2005/0221487 A1 * | 10/2005 | Zon et al. | 435/455 |
| 2006/0073591 A1 * | 4/2006 | Abitorabi et al. | 435/404 |

FOREIGN PATENT DOCUMENTS

| | | |
|---|---|---|
| EP | 0 947 581 A1 | 10/1999 |
| JP | 06-062841 A | 3/1994 |
| JP | 10-509026 A | 9/1998 |
| WO | WO 95/06112 A1 | 3/1995 |
| WO | WO 96/06928 A1 | 3/1996 |
| WO | WO 97/33978 A1 | 9/1997 |
| WO | WO 98/01151 A1 | 1/1998 |

OTHER PUBLICATIONS

Xiao et al. Cellular and Molecular aspects of human CD34+ CD38- precursors: Analysis of a primitive hematopoietic population. Leukemia Lymph 38(5-6): 489-497, 2000.*
De Bruyn et al. Characterization of CD34+ subsets derived from bone marrow, umbilical cord blood and mobilized peripheral blood after stem cell factor and interleukin 3 stimulation.Bone Marrow Transpl 25: 377-383, 2000.*
Drouet et al. Human liquid bone marrow culture in serum-free medium. Brit J Haematol 73: 143-147, 1989.*
Sandstrom et al. Review: Serum-free media for cultures of primitive and mature hematopoietic cells. Biotech Bioeng 43: 706-733, 1994.*
Chepda et al. Alpha-tocopherol as a protective agent in cell culture. In Vitro Cell Dev Biol 35: 491-492, 1999.*
Weissman et al. Stem and progenitor cells: origins, phenotypes, lineage commitments, and transdifferentiations. Annu Rev Cell Dev Biol 17: 387-403, 2001.*
Doi et al. Pluripotent hematopoietic stem cells are c-kit(low). Proc Natl Acad Sci 94: 2513-2517, 1997.*
Sogo et al. Induction of c-kit molecules on human CD34+/c-kit<low cells: evidence for CD34+/c-kit<low cells as primitive hematopoietic stem cells. Stem Cells 15: 420-429, 1997.*
Ueda et al. Expansion of human NOD/SKID-repopulating cells by stem cell factor, Flk2/Flt3 ligand, thrombopoietin, IL-6, and soluble IL-6 receptor. J Clin Invest 105: 1013-1021, 2000.*
Kobayashi et al. Thrombopoietin supports proliferation of human primitive hematopoietic cells in synergy with steel factor and/or interleukin-3. Blood 88(2): 429-436, 1996.*
Watanabe et al. In Vitro and in vivo properties of recombinant human serum albumin from *Pichia pastoris* purified by a method of short processing time. Pharmaceut Res 18(12): 1775-1781, 2001.*
Kobayashi et al. High level secretion of recombinant human serum albumin by fed-batch fermentation of the methylotrophic yeast, *Pichia pastoris*, based on optimal methanol feeding strategy. J Biosci Bioengineer 90(3): 280-288, 2000.*
Hatsuyama et al., *Rinsho Igaku*, 44(8): 229 (PS-1-1)(Aug. 2003).
Iscove et al., *Experimental Cell Research*, 126: 121-126 (1980).
Koike at al., *J. Exp. Med.*, 166: 879-890 (Sep. 1988).
StemPro-34® SFM Complete Medium Package Insert Document.
Williams et al., *Blood*, 87(5): 1687-1691 (Mar. 1, 1996).
Möbest et al., *Biotechnology and Bioengineering*, 60(3): 341-347 (1998).

* cited by examiner

*Primary Examiner* — Bridget E Bunner
(74) *Attorney, Agent, or Firm* — Leydig, Voit & Mayer, Ltd.

(57) ABSTRACT

The present invention provides useful means in an expansion culture system for a hematopoietic cell (hematopoietic stem cell, hematopoietic progenitor cell). Specifically, the present invention provides a composition for expanding a hematopoietic cell (hematopoietic stem cell, hematopoietic progenitor cell) containing recombinant human serum albumin; a serum-free medium for expanding a hematopoietic cell containing a basal medium and recombinant human serum albumin; a method of expanding a hematopoietic cell comprising culturing a hematopoietic cell in a serum-free medium containing recombinant human serum albumin, and a culture of a hematopoietic cell that can be obtained by the expansion method.

20 Claims, No Drawings

METHOD OF AMPLIFYING HEMATOPOIETIC STEM CELL AND HEMATOPOIETIC PROGENITOR CELL

TECHNICAL FIELD

The present invention relates to a composition for expanding a hematopoietic cell, a serum-free medium for expanding a hematopoietic cell, a method of expanding a hematopoietic cell, a culture of a hematopoietic cell that can be obtained by the expansion method, and the like.

BACKGROUND ART

Regeneration medicine is the area of advanced medicine that aims at repairing tissues and organs of diseased portions of the body by means of results from studies of mechanisms behind the development and organization of tissues and organs of living organisms. It is ideal that treatment be enabled by the repair capability of the patient's tissue. Hence, a likely approach to regeneration medicine is to develop a method of maximizing the potential repair capability of tissues of living organisms. To this end, it is necessary to elucidate and utilize the functions of regulators that regulate cell growth, cell differentiation, and tissue organization, such as cytokines and matrix molecules. Meanwhile, it is necessary to proliferate cells for use in transplantation therapy by in vitro culture. Hence, stem cells, which are capable of producing a wide variety of functional cells while self-proliferating for a long time, like tissue stem cells, are drawing attention.

As an example of regeneration medicine, cell medicine can be mentioned. Cell medicine refers to the art of treating disease using the patient's own tissue or another person's tissue. Cell medicine is considered to enable the proliferation of immunocytes to increase the immunizing power thereof, the cultivation of chondrocytes and transplantation thereof to joints, and the like. Among the target cells for which cell medicine is expected to be effective are hematopoietic stem cells for treating bone marrow suppression after cancer chemotherapy. Hematopoietic stem cells are used to prevent bone marrow suppression after treatment for myelocytic leukemia and cancer chemotherapy by a method comprising collecting hematopoietic stem cells from peripheral blood and the like in advance, treating them with a cell growth factor, antigen and the like, and then transplanting them.

As a representative example of cell medicine, umbilical cord blood stem cell transplantation is described below. Umbilical cord blood stem cell transplantation refers to collecting blood from the umbilical cord between the newborn and mother (umbilical cord blood), preserving it under freezing, and transplanting it to a leukemia patient and the like if necessary. Umbilical cord blood is rich in hematopoietic stem cells. Hence, hematopoietic potential is obtained even with much smaller amounts of cells than bone marrow and peripheral blood. Additionally, transplantation is possible even if there is no complete matching of HLA type, and the incidence of graft-versus-host disease (GVHD) is low. However, because the number of cells collected is limited, the currently prevalent practice is transplantation to children.

One of the essential infrastructures in regeneration medicine is the art of culturing target cells. This art is required to be of a level that ensures the proliferation (including differentiation and expansion) of target cells stably, in large amounts, at low costs, quickly, and conveniently. There are roughly two methods of cell culture: serum culture, which comprises culturing target cells using a serum-containing medium, and serum-free culture, which comprises culturing target cells using a serum-free medium, with the latter drawing attention for the reasons of the prevention of contamination with viruses and prion and the like in regeneration medicine settings. In particular, to clinically apply ex vivo expansion of umbilical cord blood, which is commonly used as a source of the cells, and the art of expansion culture of umbilical cord blood progenitor cells, it is an important task to establish a method of serum-free culture.

Regarding the expansion culture of hematopoietic cells in a serum-free medium, some related arts are known.

For example, WO98/06822 discloses a serum-free medium containing recombinant human serum albumin, but gives no description on the expansion culture of hematopoietic cells.

WO95/06112 discloses preparing hematopoietic stem cells from umbilical cord blood, and culturing them in a serum-free medium containing human serum albumin. There is also a description that cells that have been cultured under serum-free conditions tend to be undifferentiated. However, WO95/06112 essentially relates to the proliferation of neutrophil progenitor cells and megakaryocyte progenitor cells.

Furthermore, WO97/33978 discloses culturing $CD34^+$ cells prepared from umbilical cord blood in a serum-free medium containing human serum albumin, and achieving the expansion of $CD34^+$ cells by the cultivation. However, the use of recombinant human serum albumin in the cultivation is not disclosed.

DISCLOSURE OF THE INVENTION

The object of the present invention is to provide various means which are useful for an expansion culture system for a hematopoietic cell.

The present inventors investigated in consideration of the above-described circumstances, found that by using human serum albumin, a hematopoietic cell can be efficiently expanded while suppressing the differentiation of the hematopoietic cell compared to the conventional method, and developed the present invention.

Accordingly, the present invention provides the following:
(1) a composition for expanding a hematopoietic cell, which contains recombinant human serum albumin,
(2) the composition of (1) above, wherein the hematopoietic cell is a hematopoietic stem cell,
(3) the composition of (2) above, wherein the hematopoietic stem cell is selected from the group consisting of $CD34^+/CD38^-$, $CD34^+/DR^-$, $CD34^+/CD90^+$, $CD34^+/CD117^+$, $CD34^+/CD123^+$, and $CD34^+/CD133^+$,
(4) the composition of (2) above, wherein the hematopoietic stem cell is $CD34^+/CD38^-/DR^-$,
(5) the composition of (1) above, wherein the hematopoietic cell is a hematopoietic progenitor cell,
(6) a serum-free medium for expanding a hematopoietic cell, which contains a basal medium and recombinant human serum albumin,
(7) a method of expanding a hematopoietic cell, which comprises culturing a hematopoietic cell in a serum-free medium containing recombinant human serum albumin,
(8) the expansion method of (7) above, which further comprises preparing a hematopoietic cell,
(9) the expansion method of (7) or (8) above, wherein the hematopoietic cell is derived from umbilical cord blood,
(10) the expansion method of any of (7)-(9) above, wherein the hematopoietic cell is a hematopoietic stem cell,
(11) the expansion method of (10) above, wherein the expanded hematopoietic stem cell is selected from the group consisting of $CD34^+/CD38^-$, $CD34^+/DR^-$, $CD34^+/CD90^+$, $CD34^+/CD117^+$, $CD34^+/CD123^+$, and $CD34^+/CD133^+$,

(12) the expansion method of (10) above, wherein the expanded hematopoietic stem cell is CD34$^+$/CD38$^-$/DR$^-$,
(13) the expansion method of any of (7)-(9) above, wherein the hematopoietic cell is a hematopoietic progenitor cell,
(14) a culture of a hematopoietic cell that can be obtained by the method of any of (7)-(13) above, and
(15) the culture of (14) above, which does not contain a serum component.

The present invention is hereinafter described in detail.

According to the present invention, a hematopoietic cell can be expanded in a more undifferentiated state. Its expansion efficiency is much higher than that of the conventional method using a serum medium (for example, FCS-supplemented medium), a serum-free medium containing plasma-derived HSA, and the like. According to the present invention, it is possible to reduce contamination with viruses and prion, which can be problematic in cell transplantation, because it enables the expansion of a hematopoietic cell using a serum-free medium.

DETAILED DESCRIPTION OF THE INVENTION

The present invention provides a composition for expanding a hematopoietic cell, which contains recombinant human serum albumin. The composition of the present invention makes it possible to efficiently increase the number of hematopoietic cells while maintaining a more undifferentiated state than the conventional method.

As used herein, the "hematopoietic cell" refers to a hematopoietic stem cell and a hematopoietic progenitor cell, which are undifferentiated cells, and excludes differentiated cells, for example, leukocyte (e.g., granulocyte (neutrophil, eosinophil, basophil), monocyte, macrophage, lymphocyte (B cell, T cell, NK cell)), erythrocyte, and platelet. The derivation of the hematopoietic cell is a mammal, preferably a human.

The "hematopoietic stem cell" refers to a cell possessing both multipotency and renewal function, which is commonly ancestor to leukocyte, erythrocyte, platelet and the like. The hematopoietic stem cell can be CD34$^+$. Accordingly, in one aspect, CD34$^+$ cell can be used as the hematopoietic stem cell. In addition to CD34$^+$, a plurality of other hematopoietic stem cell markers can be used in combination. Examples of the stem cell marker used in combination with CD34$^+$ include CD38$^-$, DR$^-$, CD45$^+$, CD90$^+$, CD117$^+$, CD123$^+$, and CD133$^+$. Which stem cell marker hematopoietic cell is expressing can be determined by a method known per se such as a method using FACS, and a hematopoietic stem cell expressing a particular stem cell marker can be separated and purified.

The "hematopoietic progenitor cell" refers to a cell derived from a hematopoietic stem cell, and not having undergoing terminal differentiation. The hematopoietic progenitor cell can be classified into an oligopotent hematopoietic progenitor cell, which is capable of differentiating into two or three types of blood cells, and an unipotent hematopoietic progenitor cell, which differentiate into a single type of blood cell.

The hematopoietic progenitor cell can be a progenitor cell of granulocyte (eosinophil, neutrophil, and basophil), a progenitor cell of monocyte and macrophage, a progenitor cell of platelet, a progenitor cell of erythrocyte, a progenitor cell of B cell, a progenitor cell of T cell, and a progenitor cell of mast cell. The progenitor cell of platelet is preferably a progenitor cell of megakaryocyte, more preferably a progenitor cell of megakaryoblast. The progenitor cell of erythrocyte is preferably a progenitor cell of erythroblast. These series of progenitor cells can be classified by identifying the cell marker using a method known per se. For example, CD13 is known as a marker for the myelocytic lineage, CD14 as a marker for the monocytic and macrophagic lineage, CD41 as a marker for the megakaryocytic lineage, glycophorin as a marker for the erythrocytic lineage, CD19 as a marker for the B cell lineage, and CD3 as a marker for the T cell lineage.

Furthermore, the hematopoietic progenitor cell can be classified into the types of cells corresponding to the mixed colony forming unit (CFU-Mix), which is capable of differentiating into blood cell of multiple lineage; the granulocyte-macrophage colony forming unit (CFU-GM), which forms colonies of the neutrophilic and macrophagic lineage; the neutrophil colony forming unit (CFU-G); the macrophage colony forming unit (CFU-M); the erythroblast colony forming unit (CFU-E), which forms colonies and bursts of the erythroblastic lineage; the erythroblast burst forming unit (BFU-E); the megakaryocyte colony forming unit (CFU-Meg), which forms colonies and bursts of megakaryocyte; the megakaryocyte burst forming unit (BFU-Meg); the eosinophil colony forming unit (CFU-E0), the basophil colony forming unit (CFU-Baso), and the mast cell colony forming unit (CFU-Mast), which form colonies of eosinophil, basophil, and mast cell, respectively; and the like. To which colony forming unit the hematopoietic progenitor cell corresponds can be quantitatively determined by a colony assay method (in vitro colony method) known per se.

The "expansion" refers to increasing the number of what are called undifferentiated cells, which have not differentiated terminally, whereas the "proliferation" refers to increasing the total number of terminally differentiated cells and undifferentiated cells. The expansion of the hematopoietic cell can be evaluated by a cell marker analysis (for example, counting the cells corresponding to CD34$^+$ by FACS), quantitative analysis based on the colony assay method, and the like.

The recombinant human serum albumin (hereinafter abbreviated as rHSA as necessary) used in the present invention is not subject to limitation, as long as it has been prepared using gene recombination technology; for example, one that has been purified to a sufficient extent to permit its use as a pharmaceutical (injection) is preferred.

The rHSA is not subject to limitation, as long as it is an HSA produced by an HSA-producing host prepared via gene manipulation, and it is preferably one substantially free from impurity components derived from the HSA-producing host (for example, proteins, polysaccharides and the like), more preferably one prepared by culturing an rHSA-producing host by a known means, and then collecting and purifying the rHSA from the resulting culture filtrate or bacteria or cells by a known means of separation and purification. Transgenic animals and transgenic plants can also be utilized (Japanese Patent Kohyo Publication Nos. HEI-9-509565 and HEI-10-504289). Specifically, the following methods can be mentioned.

The host used to obtain rHSA in the present invention is not subject to limitation, as long as it has been prepared via gene manipulation; in addition to hosts already described in the literature, those that will be developed in the future can also be utilized as appropriate. Specifically, microorganisms (for example, *Escherichia coli*, yeasts, *Bacillus subtilis* and the like), animal cells and the like that have been rendered rHSA-producing via gene manipulation can be mentioned as examples. In particular, a yeast, preferably of the genus *Saccharomyces* [for example, *Saccharomyces cerevisiae*] or the genus *Pichia* [for example, *Pichia pastoris*], is used as the host. An auxotroph or an antibiotic-susceptible strain may be used. More suitably, the *Saccharomyces cerevisiae* AH22 strain (a, his4, leu2, can1) or the *Pichia pastoris* GTS115 strain (his4) is used.

Preparation of these rHSA-producing hosts, production of rHSA by culturing the hosts, and separation and collection of rHSA from cultures can be performed by employing known methods or methods based thereon. As examples of the method of preparing an rHSA-producing host, a method using an ordinary HSA gene (Japanese Patent Unexamined Publication Nos. SHO-58-56684, SHO-58-90515, and SHO-58-150517), a method using a novel HSA gene (Japanese Patent Unexamined Publication No. SHO-62-29985, Japanese Patent Unexamined Publication No. HEI-1-98486), a method using a synthetic signal sequence (Japanese Patent Unexamined Publication No. HEI-1-240191), a method using a serum albumin signal sequence (Japanese Patent Unexamined Publication No. HEI-2-167095), a method comprising integrating a recombinant plasmid onto chromosome (Japanese Patent Unexamined Publication No. HEI-3-72889), a method comprising fusing hosts (Japanese Patent Unexamined Publication No. HEI-3-53877), a method comprising inducing a mutation using a methanol-containing medium, a method using a mutant AOX2 promoter (Japanese Patent Unexamined Publication Nos. HEI-6-90768 and 4-299984), expression of HSA by *Bacillus subtilis* (Japanese Patent Unexamined Publication No. SHO-62-25133), expression of HSA by yeast (Japanese Patent Unexamined Publication Nos. SHO-60-41487, SHO-63-39576, and SHO-63-74493), expression of HSA by *Pichia* yeast (Japanese Patent Unexamined Publication No. HEI-2-104290) and the like can be mentioned.

Of these, the method comprising inducing a mutation using a methanol-containing medium is specifically performed as described below. First, a plasmid having a transcription unit for expressing HSA under the control of AOX1 promoter is introduced to the AOX1 gene region of an appropriate host, preferably a *Pichia* yeast, more specifically the GTS115 strain (NRRL deposit No. HEI-Y-15851), by a conventional method, to obtain a transformant (see Japanese Patent Unexamined Publication No. HEI-2-104290). This transformant is weak in proliferation potential in methanol medium. Hence, this transformant is cultured in a methanol-containing medium to induce mutations, and only those strains capable of growing in the medium are recovered. In this operation, as examples of the methanol concentration, about 0.0001 to 5% can be mentioned. The medium may be any of an artificial medium and a natural medium. As examples of the culture conditions, 15 to 40° C. and about 1 to 1000 hours can be mentioned.

As examples of the method of culturing an rHSA-producing host, in addition to the methods described in the above-mentioned patent publications, a method comprising supplying a high concentration of glucose or methanol and the like appropriately little by little by fed-batch culture (semi-batch culture) to avoid the inhibition of the producing bacteria by the high concentration substrate, and obtaining high concentrations of bacteria and the product (Japanese Patent Unexamined Publication No. HEI-3-83595), a method comprising adding a fatty acid to the medium to enhance rHSA production (Japanese Patent Unexamined Publication No. HEI-4-293495) and the like can be mentioned.

Regarding how to isolate and purify the rHSA produced by culturing treatment from components derived from host cells, culture components and the like with sufficient accuracy, various methods have been proposed. As examples of conventionally used methods, a method comprising subjecting an rHSA-containing yeast culture medium to compression→ultrafiltration membrane treatment→heat treatment→ultrafiltration membrane treatment, and then subjecting the culture medium to steps such as cation exchanger treatment, hydrophobicity chromatography treatment, and anion exchanger treatment (Japanese Patent Unexamined Publication No. HEI-5-317079; Biotechnology of Blood Proteins, Vol. 227, pp. 293-298, published in 1993) and the like can be mentioned. Methods comprising performing the above-described conventional method, and then subjecting the culture medium to a step for chelate resin treatment or boric acid/salt treatment have also been reported (Japanese Patent Unexamined Publication Nos. HEI-6-56883 and 6-245789). It is also possible to use the streamline method using adsorptive fluidized bed technology (Japanese Patent Unexamined Publication No. HEI-8-116985) and the like after the yeast culture medium is subjected to heat treatment. The rHSA thus prepared and purified can be subjected to known processes, for example, sterilization heating, ultrafiltration membrane treatment, stabilizer addition, eradication filtration, dispensing, lyophilization and other treatments.

Preparations prepared by gene recombination are considered to represent more preferable examples because of the absence of lot-to-lot differences, the ease of purification, the absence of a risk of being contaminated with virus, prion and the like, and the like.

The composition of the present invention is useful for expanding various types of human hematopoietic cell while suppressing the differentiation of the hematopoietic cell, and specifically enables the expansion of the hematopoietic stem cell from the hematopoietic stem cell, and the expansion of the hematopoietic progenitor cell from the hematopoietic stem cell and/or the hematopoietic progenitor cell.

Accordingly, in a first aspect, the composition of the present invention can be an expanding agent of the hematopoietic stem cell. For example, an rHSA-containing serum-free medium has been confirmed to expand the $CD34^+$ cell (for example, $CD34^+/CD38^-$, $CD34^+/DR^-$, $CD34^+/CD38^-/DR^-$, $CD34^+/CD90^+$, $CD34^+/CD117^+$, $CD34^+/CD123^+$, $CD34^+/CD133^+$) in a more undifferentiated state than a serum-containing medium and a serum-free medium containing plasma-derived HSA (Tables 8, 10, 16, 19, and 20). Therefore, rHSA is considered to be capable of expanding the hematopoietic stem cell in a more undifferentiated state than serum components. Accordingly, the composition of the present invention can be used to expand the hematopoietic stem cell in a more undifferentiated state.

An rHSA-containing serum-free medium has been confirmed to more efficiently expand the $CD34^+/CD38^-$ cell and $CD34^+/CD38^-/DR^-$ cell than a serum-containing medium (Table 2). Therefore, rHSA is considered to be capable of more efficiently expanding the $CD34^+/CD38^-$ cell and/or $CD34^+/CD38^-/DR^-$ cell than serum components and plasma-derived HSA. Accordingly, the composition of the present invention can be used to more efficiently expand the $CD34^+/CD38^-$ cell and/or the $CD34^+/CD38^-/DR^-$ cell.

In another aspect, the composition of the present invention can be an expanding agent of the hematopoietic progenitor cell. For example, the serum-free medium containing rHSA has been shown to tend to more selectively expand the cell corresponding to CFU-Mix or BFU-E than a serum-containing medium (Tables 3 and 18). Therefore, rHSA is likely to more selectively expand the cell corresponding to CFU-Mix or BFU-E than serum components. Accordingly, the composition of the present invention can be used to more selectively expand the cell corresponding to CFU-Mix or BFU-E.

The serum-free medium containing rHSA has also been confirmed to more expand the cell corresponding to CFU- Mix, CFU-GM or BFU-E than a serum-free medium containing plasma-derived HSA (see Tables 14 and 15). Therefore, rHSA is considered to be capable of expanding the cell corresponding to CFU-Mix, CFU-GM or BFU-E than plasma-derived HSA. Accordingly, the composition of the present invention can be used to expand the cell corresponding to CFU-Mix, CFU-GM or BFU-E.

Furthermore, the serum-free medium containing rHSA has been confirmed to expand the blood progenitor cell from the hematopoietic cell while maintaining a more undifferentiated state than a serum-containing medium (Tables 4, 5, and 20). Therefore, rHSA is considered to be capable of more suppressing the differentiation of the hematopoietic cell during expansion of the hematopoietic cell than serum components. Accordingly, the composition of the present invention can be used to expand the hematopoietic progenitor cell in a more undifferentiated state.

Furthermore, the serum-free medium containing rHSA has been confirmed to more suppress the differentiation to the neutrophilic lineage cell from the hematopoietic cell than the serum-containing medium (Tables 6 and 7). Therefore, rHSA is considered to be capable of more suppressing the differentiation to the neutrophilic lineage cell from the hematopoietic cell during the expansion of the hematopoietic cell than serum components. Accordingly, the composition of the present invention can be used to suppress the expansion of the neutrophilic lineage cell from the hematopoietic cell.

The serum-free medium containing rHSA has also been confirmed to more suppress the differentiation to the monocytic and macrophagic lineage cell from the hematopoietic cell than the serum-containing medium (Tables 9 and 21). Therefore, rHSA is considered to be capable of more suppressing the differentiation to the monocytic and macrophagic lineage cell from the hematopoietic cell during the expansion of the hematopoietic cell than serum components. Accordingly, the composition of the present invention can be used to suppress the expansion of the monocytic and macrophagic lineage cell from the hematopoietic cell.

The composition of the present invention contains rHSA and a carrier. Preferably, the carrier can be a pharmaceutically acceptable carrier. As the pharmaceutically acceptable carrier, excipients, diluents, fillers, disintegrants, stabilizers, preservatives, buffering agents, emulsifiers, flavoring agents, coloring agents, sweetening agents, thickening agents, taste correctives, solubilizers or other additives and the like can be mentioned. By using one or more of such carriers, a pharmaceutical composition in the form of an injection, liquid and the like can be prepared.

In particular, an injection can be produced by, for example, dissolving or suspending the active ingredient in a non-toxic pharmaceutically acceptable carrier such as physiological saline or commercially available distilled water for injection to obtain an appropriate concentration. In some cases, an injection can also be prepared in a non-aqueous diluent (for example, propylene glycol, polyethylene glycol, vegetable oils such as olive oil, alcohols such as ethanol, and the like), suspending agent or emulsifier.

Sterilization of such an injection can be achieved by filtration sterilization through a bacterial retention filter, combining with a bactericidal agent, or irradiation. An injection can be produced as a fresh supply prepared before use. Specifically, the injection can be prepared as a sterile solid composition by lyophilization and the like, which composition can be used after being freshly dissolved in sterile distilled water for injection or another solvent.

The composition of the present invention can contains a lipid, various vitamins, and other components as necessary. As examples of the lipid, cholesterol, lecithin (phospholipid) and the like can be mentioned. As examples of the vitamins, vitamin C (ascorbic acid), vitamin E (tocopherol) and the like can be mentioned. As examples of the other components, growth factors such as insulin, iron sources such as transferrin, various cytokines and the like can be mentioned. As examples of the cytokines, SCF, TPO (thrombopoietin), FL (Flt3/Flk2 ligand), IL6, IL6R (IL6 receptor) and the like can be mentioned.

The present invention also provides a serum-free medium for expanding the hematopoietic cell, containing a basal medium and recombinant human serum albumin. The serum-free medium of the present invention characteristically contains a basal medium and rHSA. The rHSA added to the serum-free medium of the present invention is as described above.

The basal medium used to prepare the serum-free medium of the present invention is not subject to limitation, as long as it is one used for ordinary cell culture, particularly for mammalian cell culture. Specifically, MEM (αMEM and the like), RPMI (RPMI1640 and the like), and HamF (HamF12 and the like) can be mentioned.

The amount of recombinant HSA added to the serum-free medium of the present invention is not subject to limitation, as long as the efficient expansion of the hematopoietic cell and/or the selective expansion of particular hematopoietic cell is enabled, and it is, for example, about 0.1 to 20 w/v %, preferably about 0.5 to 10 w/v %, and more preferably about 1 to 5 w/v %.

A lipid is added to the serum-free medium of the present invention as necessary. As examples of the lipid added to the serum-free medium of the present invention, cholesterol, lecithin (phospholipid) and the like can be mentioned. The amount of cholesterol added is, for example, about 10 to 1000 μg/ml, and the amount of lecithin added is, for example, about 10 to 1000 μg/ml.

The serum-free medium of the present invention may further be supplemented with other component. As examples of the other components, growth factors such as insulin, iron sources such as transferrin, various cytokines and the like can be mentioned. As examples of the cytokines, SCF, TPO (thrombopoietin), FL (Flt3/Flk2 ligand), IL6, IL6R (IL6 receptor) and the like can be mentioned. As examples of the amount of insulin added, 0.1 to 100 units (as quantified by rabbit blood glucose levels) or about 0.1 to 100 μg/ml can be mentioned. As examples of the amount of transferrin added, about 10 to 1000 μg/ml can be mentioned. As examples of the amounts of cytokines added, about 1 to 1000 ng/ml, preferably about 10 to 100 ng/ml, for each cytokine, can be mentioned.

Furthermore, various vitamins and the like are added to the serum-free medium of the present invention as necessary. As examples of the vitamins added, vitamin C (ascorbic acid), vitamin E (tocopherol) and the like can be mentioned. The amount of vitamins added can be, for example, about 0.1 to 10 μg/ml.

The pH of the serum-free medium of the present invention is not subject to limitation, as long as the expansion of the hematopoietic cell is enabled, and it is, for example, about 6.0 to 8.0, preferably about 6.8 to 7.6, and most preferably about 7.0 to 7.2.

The serum-free medium of the present invention is useful for enabling the expansion of generic hematopoietic cell while maintaining the hematopoietic cell in a more undifferentiated state; specifically, the expansion of the hematopoietic stem cell from the hematopoietic stem cell, and the expansion of the hematopoietic progenitor cell from the hematopoietic stem cell and/or the hematopoietic progenitor cell are enabled.

Accordingly, in a first aspect, the serum-free medium of the present invention can be a medium for expanding the hematopoietic stem cell. For example, the serum-free medium containing rHSA has been confirmed to expand the $CD34^+$ cell (for example, $CD34^+/CD38^-$, $CD34^+/DR^-$, $CD34^+/CD38^-/DR^-$, $CD34^+/CD90^+$, $CD34^+/CD117^+$, $CD34^+/CD123^+$, $CD34^+/CD133^+$) in a more undifferentiated state than a serum-containing medium and a serum-free medium containing plasma-derived HSA (Tables 8, 10, and 16). Accordingly, the serum-free medium of the present invention can be used to expand the hematopoietic stem cell in a more undifferentiated state.

The serum-free medium containing rHSA has also been confirmed to more efficiently expand the $CD34^+/CD38^-$ cell and the $CD34^+/CD38^-/DR^-$ cell than a serum-containing medium (Table 2). Accordingly, the serum-free medium of the present invention can be used to more efficiently expand the $CD34^+/CD38^-$ cell and/or the $CD34^+/CD38^-/DR^-$ cell.

In another aspect, the serum-free medium of the present invention can be a medium for expanding the hematopoietic progenitor cell. For example, the serum-free medium containing rHSA has been shown to tend to more selectively expand the cell corresponding to CFU-Mix or BFU-E than a serum-containing medium (Table 3). Accordingly, the composition of the present invention can be used to more selectively expand the cell corresponding to CFU-Mix or BFU-E.

The serum-free medium containing rHSA has also been confirmed to more expand the cell corresponding to CFU-Mix, CFU-GM or BFU-E than a serum-free medium containing plasma-derived HSA (see Tables 14 and 15). Accordingly, the serum-free medium of the present invention can be used to expand the cell corresponding to CFU-Mix, CFU-GM or BFU-E.

Furthermore, the serum-free medium containing rHSA has been confirmed to expand the blood progenitor cell from the hematopoietic cell while maintaining a more undifferentiated state than a serum-containing medium (Tables 4 and 5). Accordingly, the serum-free medium of the present invention can be used to expand the hematopoietic progenitor cell in a more undifferentiated state.

Furthermore, the serum-free medium containing rHSA has been confirmed to more suppress the differentiation to the neutrophilic lineage cell from the hematopoietic cell than a serum-containing medium (Tables 6 and 7). Accordingly, the serum-free medium of the present invention can be used to suppress the differentiation to the neutrophilic lineage cell from the hematopoietic cell.

The serum-free medium containing rHSA has also been confirmed to more suppress the differentiation to the monocytic and macrophagic lineage cell from the hematopoietic cell than a serum-containing medium (Table 9). Accordingly, the serum-free medium of the present invention can be used to suppress the differentiation to the monocytic and macrophagic lineage cell from the hematopoietic cell.

The present invention further provides a method of expanding the hematopoietic cell, comprising culturing the hematopoietic cell in a serum-free medium containing recombinant human serum albumin. The human serum albumin and the serum-free medium are the same as those described above.

The hematopoietic cell used in the expansion method of the present invention may be any available cells, and can be exemplified by a hematopoietic cell prepared from umbilical cord blood, peripheral blood, bone marrow and the like. These hematopoietic cells can be used after being purified to $CD34^+$ by a method known per se.

The amount of cells seeded to the serum-free medium is not subject to limitation, as long as culture of the hematopoietic cell is enabled, and it is exemplified by about $1\times10^4$ to $1\times10^5$ cells/ml. Although duration of cultivation is not subject to limitation, it is exemplified by 1 day or more (for example, 1 to 20 days), preferably 7 days or more (for example, 7 to 14 days). Culturing temperature can be about 30 to 40° C., preferably 37° C. As examples of the carbon dioxide content, about 1 to 10%, preferably about 5% and the like can be mentioned.

The expansion method of the present invention is useful for enabling the expansion of generic hematopoietic cell while maintaining the hematopoietic cell in a more undifferentiated state; specifically, the expansion of hematopoietic stem cell from hematopoietic stem cell, and the expansion of hematopoietic progenitor cell from the hematopoietic stem cell and/or the hematopoietic progenitor cell are enabled.

The expansion method of the present invention comprises using a serum-free medium containing rHSA. Accordingly, in one aspect, the expansion method of the present invention enable the expansion of the hematopoietic stem cell in a more undifferentiated state than culture using a serum-containing medium and a serum-free medium containing plasma-derived HSA. The expansion method of the present invention also enables the more efficient expansion of the $CD34^+/CD38^-$ cell and/or the $CD34^+/CD38^-/DR^-$ cell than culture using a serum-containing medium.

In another aspect, the expansion method of the present invention enables the more selective expansion of the cell corresponding to CFU-Mix or BFU-E than the method using a serum-containing medium. The expansion method of the present invention also enables the more expansion of the cell corresponding to CFU-Mix, CFU-GM or BFU-E than a serum-free medium containing plasma-derived HSA. Furthermore, the expansion method of the present invention enables the expansion of the hematopoietic progenitor cell in a more undifferentiated state than a serum-containing medium. The expansion method of the present invention enables the more suppression of the expansion of the neutrophilic lineage cell from the hematopoietic cell than a serum-containing medium. Furthermore, the expansion method of the present invention enables the more suppression of the expansion of the monocytic and macrophagic lineage cell from the hematopoietic cell than a serum-containing medium.

The present invention also provides a culture of the hematopoietic cell that can be obtained by the above-described expansion method of the present invention. Because the culture of the present invention is obtained by culturing the hematopoietic cell using a serum-free medium containing rHSA, it does not contain a serum-derived component. Accordingly, the culture of the present invention is useful for use in cell medicine and the like because it is free from the concern about contamination with harmful substances such as viruses and prion derived from serum components.

The culture of the hematopoietic cell of the present invention may be present in the culture medium, or may be provided in a form recovered by a method known per se such as centrifugation. The culture can be purified into the hematopoietic stem cell by a method known per se such as FACS with a marker such as $CD34^+$ as the index. The culture can also be purified into the hematopoietic progenitor cell, preferably particular the hematopoietic progenitor cell, using various markers (for example, CD13, CD14, CD41, glycophorin, CD19, CD3) for the hematopoietic progenitor cell. Accordingly, the present invention also provides a culture of the hematopoietic stem cell that can be obtained by the culture method of the present invention, and a culture of generic hematopoietic progenitor cell and of particular hematopoietic progenitor cell.

EXAMPLES

The present invention is hereinafter described in more detail by means of the following working examples and experimental examples, which, however, are not to be construed as limiting the scope of the invention.

Reference Example 1

Preparation of rHSA rHSA was prepared as described below. First, the rHSA-producing yeast *Pichia pastoris* was obtained and cultured in accordance with the method described in Japanese Patent Unexamined Publication No. HEI-5-317079. rHSA was recovered and purified from the culture broth obtained, in accordance with the method described in Japanese Patent Unexamined Publication No. HEI-8-116985. Then, the purified rHSA was prepared as a 25% solution.

Subsequently, the properties of the purified rHSA (-containing composition) were confirmed by the respective analytical methods shown below. The results of these measurements of the properties are shown in Table 1.

HPLC Analysis:

The rHSA was analyzed by HPLC gel filtration. The column used was TSK gel G3000SW (Tosoh Corporation), the developing solution used was 0.1 M $KH_2PO_4$/0.3 M NaCl buffer, and the detection was achieved using absorbance at a wavelength of 280 nm.

Analysis of Yeast-Derived Components:

Rabbits were immunized with a supernatant of non-HSA-producing yeast, crudely purified by the above-described method, and yeast-derived components occurring as impurities in the purified rHSA-containing composition were detected using the antiserum thus obtained. Measurements were taken by enzyme immunoassay (EIA method). The supernatant used for the measurements was prepared to an rHSA concentration of 25%.

Molecular Weight:

Determined in the same manner as the HPLC gel filtration described above.

Isoelectric Point:

Measured using a thin-layer polyacrylamide gel in accordance with the method of Allen et al. (J. Chromatog., 146, p. 1, 1978).

Degree of Coloring:

Absorbances at wavelengths of 280 nm, 350 nm, 450 nm and 500 nm were determined, and $A_{350}/A_{280}$, $A_{450}/A_{280}$, and $A_{500}/A_{280}$ were calculated respectively.

Pyrogen:

Endospecy from Seikagaku Corporation was used.

TABLE 1

| Properties of Recombinant HSA (-comprising Composition) | |
|---|---|
| Analytical item | Results |
| HPLC | Single peak of HSA monomer |
| Yeast-derived components | |
| (based on proteins) | less than 0.1 ng/mL |
| (based on polysaccharides) | less than 1 ng/mL |

TABLE 1-continued

| Properties of Recombinant HSA (-comprising Composition) | |
|---|---|
| Analytical item | Results |
| Molecular weight | Approx. 67000 |
| Isoelectric point | Approx. 4.9 |
| Degree of coloring ($A_{350}/A_{280}$) | Approx. 0.015 |
| ($A_{450}/A_{280}$) | Approx. 0.01 |
| ($A_{500}/A_{280}$) | Approx. 0.002 |
| Pyrogen | less than 0.5 EU (per 250 mg rHSA) |

The composition containing rHSA was used in the working examples and experimental examples of the present invention.

Example 1

Preparation of a Serum-Free Medium Containing rHSA

αMEM, 2 w/v % rHSA, 100 μg/ml cholesterol (ICN Biomedical Company), 160 μg/ml lecithin (ICN Biomedical Company), 1 μg/ml insulin (Sigma Company), 200 μg/ml holotransferrin (Sigma Company), 1 μg/ml tocopherol (WAKO Company), and 1 μg/ml ascorbic acid (WAKO Company) were combined to prepare a complete serum-free medium. Since cholesterol is slightly soluble, it was dissolved in ethanol, after which the solution was stirred using a stirrer with a temperature setting of 30 to 40° C. for 10 minutes to evaporate the ethanol. Thereafter, the solution was transferred to a normal-temperature stirrer, and the rHSA was gradually added drop by drop to cause conjugation before the cholesterol crystallized. After the above-described reagents were mixed with this solution, filtration sterilization was performed using a bottle-top filter. Alternatively, another method was used as described below. Specifically, each of cholesterol, lecithin, and tocopherol was dissolved in ethanol, and required amounts of the cholesterol solution, lecithin solution, and tocopherol solution thus prepared were transferred to a flask and mixed and stirred. With stirring using a stirrer, the rHSA was gradually added drop by drop. A white precipitate was produced; after this was mixed with the rHSA, all the rHSA was added drop by drop at a slightly increased rate. This mixture was stirred using a stirrer for about 10 minutes. Furthermore, after the above-described reagents were mixed in this solution, filtration sterilization was performed.

Example 2

Preparation of a Serum-Free Medium Containing rHSA and Various Cytokines

αMEM, 2 w/v % rHSA, 100 μg/ml cholesterol (ICN Biomedical Company), 160 μg/ml lecithin (ICN Biomedical Company), 1 μg/ml insulin (Sigma Company), 200 μg/ml holotransferrin (Sigma Company), 1 μg/ml tocopherol (WAKO Company), 1 μg/ml ascorbic acid (WAKO Company), 100 ng/ml SCF, 10 ng/ml TPO, 100 ng/ml FL, 100 ng/ml IL6, and 100 ng/ml sIL6R were combined to prepare a complete serum-free medium.

Experimental Example 1

Measurement of Expansion Rates of Umbilical Blood CD34[+] Cells

Expansion rates of cultured CD34[+] cells in a serum medium and a serum-free medium were analyzed on days 7 and 14 of cultivation. The $CD34^+$ cell expansion rate is the ratio of the $CD34^+/CD45^+$ cell count on day 7 or 14 to the $CD34^+/CD45^+$ cell count on day 0, based on FACS analysis. The expansion rates of $CD34^+/CD38^-$ cells and $CD34^+/CD38^-/DR^-$ cells are the ratios of the $CD34^+/CD38^-$ cell count and $CD34^+/CD38^-/DR^-$ cell count on day 7 or 14, to the $CD34^+/CD38^-$ cell count and $CD34^+/CD38^-/DR^-$ cell count on day 0, respectively, based on FACS analysis. The medium, $CD34^+$ cells, and culturing conditions used are as described below. The results are shown in Table 2.

Medium:

The serum medium used was an αMEM (minimal essential medium α) supplemented with 10% or 20% FCS (fetal calf serum, JRH Company) and five kinds of cytokines (100 ng/ml SCF, 10 ng/ml TPO, 100 ng/ml FL, 100 ng/ml IL6, and 100 ng/ml sIL6R), and the serum-free medium used was the same as that prepared in Example 2.

$CD34^+$ Cells:

$CD34^+$ cells stored under freezing with liquid nitrogen after being separated from umbilical cord blood using the magnet immunobead method (AutoMACS) were used after thawing. The purity of the $CD34^+$ cells used was not less than 95%.

Culturing Conditions:

$1 \times 10^4$ $CD34^+$ cells were seeded to 1 ml of each of a serum medium and serum-free medium prepared as described above, and cultured in a 5% $CO_2$ incubator for 7 days or 14 days. The cultivation was performed using 24-well plates.

TABLE 2

FACS Analysis of Expansion Rates by Cultivation

| | | Expansion rate | | | |
|---|---|---|---|---|---|
| | Medium | Day 0 | Day 7 | Day 14 | P value |
| Total cells | FCS | 1 | 62 | 298 | 0.00774 |
| | Serum-free | 1 | 9 | 66 | |
| $CD34^+$ cell | FCS | 1 | 21 | 65 | 0.176 |
| | Serum-free | 1 | 7 | 29 | |
| $CD34^+/CD38^-$ cell | FCS | 1 | 11 | 30 | 0.0463 |
| | Serum-free | 1 | 4 | 39 | |
| $CD34^+/CD38^-/DR^-$ cell | FCS | 1 | 11190 | 12887 | 0.0464 |
| | Serum-free | 1 | 6418 | 70625 | |

As a result, the total cell proliferation rate was higher for the serum medium than for the serum-free medium, whereas the expansion rates of $CD34^+/CD38$ cells and $CD34^+/CD38^-/DR^-$ cells on day 14 were higher for the serum-free medium than for the serum medium (Table 2).

From these results, it was demonstrated that the serum-free medium containing rHSA was inferior to the serum medium in terms of total cell expansion rate but superior to the serum medium in terms of the selective expansion of $CD34^+/CD38^-$ cells and $CD34^+/CD38^-/DR^-$ cells in long-term culture.

Experimental Example 2

Measurement of Colony Formation Potential of Cultured Cells

The colony formation potential of cultured $CD34^+$ cells was analyzed in a serum medium and a serum-free medium on days 7 and 14 of cultivation. The medium, $CD34^+$ cells, and culturing conditions used were the same as those in Experimental Example 1. The colony formation potential was evaluated by colony assay. Specifically, the colony assay was performed using a methyl cellulose medium (MethoCult Company) before culture and on days 7 and 14 of cultivation. Cells were seeded at a cell density of 250 cells/dish before culture and on day 7 of cultivation, and at 500 cells/dish on day 14 of cultivation; after 14 days of cultivation, colonies were counted. The total colony count expansion rate was obtained by calculating the number of colony forming cells from the total colony count per unit and the total cultured cell count, and converting it to a multiplication factor. The CFU-GM, BFU-E, and CFU-Mix expansion rates were obtained by calculating the number of colony forming cells from the CFU-GM, BFU-E, and CFU-Mix colony forming rates, respectively, per unit and the total cell count, and converting it to a multiplication factor. The results are shown in Table 3.

TABLE 3

Colony Assay Analysis of Expansion Rate by Cultivation

| | | Expansion rate | | | |
|---|---|---|---|---|---|
| Cells evaluated | Medium | Day 0 | Day 7 | Day 14 | P value |
| Total cells | FCS | 1 | 21.3 | 69.0 | 0.284 |
| | Serum-free | 1 | 10.0 | 20.9 | |
| CFU-GM | FCS | 1 | 27.2 | 90.2 | 0.824 |
| | Serum-free | 1 | 10.8 | 24.1 | |
| BFU-E | FCS | 1 | 3.0 | 1.5 | 0.307 |
| | Serum-free | 1 | 8.2 | 11.6 | |
| CFU-Mix | FCS | 1 | 2.1 | 2.8 | 0.15 |
| | Serum-free | 1 | 5.5 | 8.3 | |

As a result, the CFU-GM expansion rate was higher for the serum-free medium than for the serum medium, whereas the BFU-E and CFU-Mix expansion rates were higher for the serum-free medium than for the serum medium (Table 3).

From these results, it was demonstrated that the serum-free medium containing rHSA tended to be inferior to the serum medium in terms of total cell and CFU-GM expansion rates, but superior to the serum medium in terms of the selective expansion of BFU-E and CFU-Mix.

Experimental Example 3

Morphological Analysis of Cultured $CD34^+$ Cells by Staining $CD34^+$ cells on day 14 of cultivation were morphologically analyzed by three kinds of staining, i.e., May-Giemsa, peroxidase, and esterase, as reported previously. The morphological classification of cultured cells by Giemsa staining is shown in Table 4; a list of cells classified by the same staining is shown in Table 5; the morphological classification of cultured cells by peroxidase staining is shown in Table 6; the morphological classification of cultured cells by esterase staining is shown in Table 7.

TABLE 4

Morphological Classification of Cultured Cells by Giemsa Staining

| | FCS | Serum-free | Serum-free/FCS |
|---|---|---|---|
| Blast | 25 | 80 | 3.2 |
| Mature cell | 67 | 19 | — |

TABLE 5

List of Cells Classified by Giemsa Staining

|   |   | FCS | Serum-free |
|---|---|---|---|
| myeloid | myeloblast | 25 | 80 |
|  | promyelocyte | 67 | 19 |
|  | myelocyte | 0 | 0 |
|  | metamyelocyte | 0 | 0 |
| mono | monoblast | 0 | 1 |
|  | monocyte | 6 | 0 |
|  | macropharge | 2 | 0 |
|  | erythroid cell | 0 | 0 |
|  | megakaryocyte | 0 | 0 |

TABLE 6

Morphological Classification of Cultured Cells by Peroxidase Staining

|  | FCS | Serum-free | Serum-free/FCS |
|---|---|---|---|
| Negative | 50 | 71 | 1.42 |
| False positive | 14 | 5 | — |
| Positive | 36 | 24 | — |

TABLE 7

Morphological Classification of Cultured Cells by Esterase Staining

|  | FCS | Serum-free | Serum-free/FCS |
|---|---|---|---|
| Negative | 53 | 79 | 1.49 |
| Positive for specific esterase (AS-D) | 39 | 12 | — |
| Positive for nonspecific esterase (α-NB) | 8 | 8 | — |

As a result, the analysis by Giemsa staining revealed that the serum-free medium maintained a more undifferentiated state than the serum medium (Table 4). In particular, the ratio of myeloblasts was higher for the serum-free medium than for the serum medium (Table 5). The analyses by peroxidase staining and specific esterase staining (peroxidase-positive cells and specific esterase-positive cells mainly differentiate into the neutrophilic lineage cells) revealed that the serum-free medium more suppressed the differentiation of CD34$^+$ cells into the neutrophilic lineage cells during expansion thereof than the serum medium (Tables 6 and 7).

From these results, it was demonstrated that the CD34$^+$ cells cultured using the serum-free medium containing rHSA maintained higher immaturity than the CD34$^+$ cells cultured using a serum medium.

Experimental Example 4

Analyses of Surface Antigens of Cultured Cells

Surface antigens of cultured CD34$^+$ cells were analyzed in a serum medium and a serum-free medium on day 14 of cultivation. The medium, CD34$^+$ cells, and culturing conditions used were the same as those in Experimental Example 1. The cultured cells were subjected to trichromic staining by a conventional method, and surface antigens were then analyzed using a FACS Calibur. As surface antigen analyses, CD34$^+$/CD38$^-$/DR$^-$ positivity rate analysis, hematopoietic progenitor cell property analysis, and lineage analysis were performed. The antibodies used in this analysis were antibodies against the markers shown below.

CD34$^+$/CD38$^-$/DR$^-$ cell positivity rate: CD34, CD38, and HLA-DR

Lineage analysis: CD13 (a marker for the myelocytic lineage), CD14 (a marker for the monocytic and macrophagic lineage), CD41 (a marker for the megakaryocytic lineage), CD19 (a marker for the B cell lineage), CD3 (a marker for the T cell lineage), and glycophorin (a marker for the erythrocytic lineage)

Hematopoietic progenitor cell property analysis: CD90, CD117, CD38, HLA-DR, CD123, and CD133

The CD34$^+$/CD38$^-$/DR$^-$ cell positivity rate analysis was performed using FACS as described below. First, a population of cells obtained from scatter grams of forward scatter (FS) and side scatter (SS) were gated (R1). Subsequently, the SS and CD34$^+$ regions were gated (R2). Furthermore, the cells within the R1 and R2 gates were developed with CD38 and HLA-DR (34 gating). Subsequently, the average value (n=5) for the 34 gating CD38$^-$/DR$^-$ was calculated.

The results for the CD34$^+$/CD38$^-$/DR$^-$ cell positivity rate are shown in Table 8; the results for the lineage analysis are shown in Table 9; the results for the hematopoietic stem cell property analysis are shown in Table 10.

TABLE 8

Ratio of CD34$^+$/CD38$^-$/DR$^-$ cells to CD34$^+$ cells

| Medium | Ratio (%) |
|---|---|
| FCS | 2.6 ± 1.7 |
| Serum-free | 21.4 ± 4.8 |

TABLE 9

Lineage Analysis of Cultured Cells on Day 14 of Cultivation

|  | FCS | Serum-free | P value |
|---|---|---|---|
| CD3 | 9.48 | 5.37 | 0.436 |
| Glycophorin | 0.51 | 3.39 | 0.26 |
| CD19 | 2.77 | 6.82 | 0.486 |
| CD41 | 0.66 | 3.79 | 0.492 |
| CD14 | 41.04 | 17.91 | 0.000912 |
| CD13 | 95.50 | 97.36 | 0.568 |

TABLE 10

Analysis of Stem Cell Markers

|  | Stem cell marker expression rate (%) | | |
|---|---|---|---|
| Stem cell marker | FCS | Serum-free | P value |
| CD34$^+$/CD133$^+$ | 7.7 | 37.7 | 0.00379 |
| CD34$^+$/CD123$^+$ | 9.6 | 24.2 | 0.0268 |
| CD34$^+$/CD117$^+$ | 1.5 | 5.2 | 0.0434 |
| CD34$^+$/CD90$^+$ | 0.1 | 0.4 | 0.0666 |
| CD34$^+$/DR$^-$ | 2.6 | 21.4 | 0.0156 |
| CD34$^+$/CD38$^-$ | 11.6 | 60.6 | 0.0000939 |

As a result, the ratio of CD34$^+$/CD38$^-$/DR$^-$ cells in CD34$^+$ cells was about 8 time higher for the serum-free medium than for the serum medium. The lineage analysis revealed that the serum-free medium more suppressed the differentiation of CD34$^+$ cells into the monocytic lineage than the serum medium (Table 9). Furthermore, the hematopoietic stem cell marker analysis revealed that all markers were highly expressed in the serum-free culture, with all markers but CD34+/CD90+ being significantly highly expressed (Table 10).

From these results, it was demonstrated that the serum-free medium containing rHSA is superior to the serum medium in terms of the selective expansion of CD34+ cells to CD34+/CD38−/DR− cells, that it more suppresses the differentiation of CD34+ cells into the monocytic lineage cells during the expansion thereof than the serum medium, and that it is superior to the serum medium in terms of the undifferentiated expansion of hematopoietic stem cells.

Experimental Example 5

Measurement of Cytokine Contents in Culture Medium

Since the cultured cell colony formation rate was better for the serum-free medium in Experimental Example 2, it was speculated that serum-free culture more selectively expands hematopoietic progenitor cells, which possess self-replication potential, rather than differentiation potential. Since the presence of a differentiation-promoting cytokine in FCS was considered as a cause of this finding, the cytokine contents in the culture medium, and the cytokine contents in the culture supernatant on day 14 of cultivation were measured by the ELISA method. These measurements were taken for G-CSF, GM-CSF, TGF-β1, TGF-β2, IL3, and EPO. The results for the cytokine contents in the culture medium are shown in Table 11; the results for the cytokine contents in the culture supernatant are shown in Table 12.

TABLE 11

Cytokine Contents of Culture medium

| | FCS | Serum-free | Significant difference |
|---|---|---|---|
| G-CSF (pg/ml) | — | — | — |
| GM-CSF (pg/ml) | <0.9 | <0.9 | NS |
| TGF-β1 (pg/ml) | — | — | — |
| TGF-β2 (pg/ml) | 104.93 | <1 | P < 0.0001 |
| EPO (mUnit/ml) | <1 | <1 | NS |
| IL3 (pg/ml) | <1 | <1 | NS |

NS indicates the absence of significant difference.

TABLE 12

Cytokine Contents of Culture Supernatant on Day 14 of Cultivation

| | FCS | Serum-free | Significant difference |
|---|---|---|---|
| G-CSF (pg/ml) | <4 | <4 | NS |
| GM-CSF (pg/ml) | 1.31 ± 0.45 | 0.61 ± 0.18 | P = 0.0406 |
| TGF-β1 (pg/ml) | 6.25 ± 0.5 | 6.25 ± 0.5 | NS |
| TGF-β2 (pg/ml) | 115.05 ± 13.20 | <1 | P < 0.00002 |
| EPO (mUnit/ml) | 4.80 ± 4.55 | <1 | P < 0.01 |
| IL3 (pg/ml) | <1 | <1 | NS |

NS indicates the absence of significant difference.

As a result, it was found that GM-CSF, TGF-β2, and EPO were significantly more abundant with the serum culture. When the culture medium were assayed, TGF-β2 was detected only in the case of the serum medium (Table 11). With the serum culture, TGF-β2 was detected at high concentrations. TGF-β2 has been reported to be effective in enhancing the expression of differentiation type cytokine receptors for highly differentiated hematopoietic cells, and hence to stimulate the secretion of differentiation type cytokines; in the present investigation, differentiation type cytokines such as GM-CSF increased significantly in the culture supernatant of the serum culture on day 14 of cultivation.

From these results, it was demonstrated that the serum-free medium of the present invention is useful in expanding hematopoietic stem cells and hematopoietic progenitor cells, which have self-replication potential.

Experimental Example 6

Comparison of Potency Between Plasma-Derived HSA and rHSA 6.1. Preparation of a Serum-Free Medium Containing Plasma-Derived HSA The method of cultivation, medium composition, method of surface antigen analysis, and colony assay method used were the same as those in Experimental Example 1. A medium supplemented with plasma-derived HAS was prepared as a serum-free medium by combining αMEM, 2 w/v % human plasma-derived HSA (manufactured by Mitsubishi Pharma Corporation), 100 μg/ml cholesterol (manufactured by ICN Biomedical Company), 160 μg/ml lecithin (manufactured by ICN Biomedical Company), 1 μg/ml insulin (manufactured by Sigma Company), 100 ng/ml SCF, 10 ng/ml TPO, 100 ng/ml FL, 100 ng/ml IL6, and 100 ng/ml sIL6R.

6.2. Comparison of Expansion of CD34+ Cells $10^4$ of CD34+ cells were seeded to each medium. Vitamin E and vitamin C were added to each serum-free medium containing plasma-derived HSA or rHSA. Total cultured cell counts on day 14 of cultivation were measured. The results are shown in Table 13.

TABLE 13

Expansion of CD34+ cells

| | Total number of cultured cells ($\times 10^4$) |
|---|---|
| Day 0 | 1 |
| FCS | 640 |
| Plasma-derived HSA | 120 |
| Recombinant HSA | 80 |

6.3. Comparison of Colony Formation Potentials

After 14 days of cultivation in the same manner as in Experimental Example 2, colony formation potentials on days 7 and 14 of cultivation was analyzed. The colony forming potential on day 7 of cultivation is shown in Table 14; the colony formation potential on day 14 of cultivation is shown in Table 15.

TABLE 14

Colony Formation Potential on Day 7 of Cultivation

| | Fresh | FCS | Plasma-derived HSA | Recombinant HSA |
|---|---|---|---|---|
| CFU-GM | 175 | 115 | 165 | 215 |
| BFU-E | 59 | 5 | 33 | 32 |
| CFU-Mix | 28 | 0 | 7 | 21 |
| Total count | 262 | 120 | 205 | 268 |

TABLE 15

Colony Formation Potential on Day 14 of Cultivation

|  | Fresh | FCS | Plasma-derived HSA | Recombinant HSA |
|---|---|---|---|---|
| CFU-GM | 175 | 131 | 96 | 150 |
| BFU-E | 59 | 1 | 7 | 23 |
| CFU-Mix | 28 | 0 | 1 | 8 |
| Total count | 262 | 132 | 104 | 181 |

6.4. Comparison of Expansion of CD34$^+$/CD38$^-$ Cells

Analyzed using FACS in the same manner as described above. After 14 days of cultivation, both the CD34 and CD38 antigens were analyzed. The results are shown in Table 16.

TABLE 16

Anaylsis of Surface Antigens CD34 and CD38 on Day 14 of Cultivation

| Cell | FCS | Plasma-derived HSA | Recombinant HSA |
|---|---|---|---|
| CD34$^+$/CD38$^-$ | 1.1% | 9.8% | 17.6% |
| CD34$^+$/CD38$^+$ | 13.8% | 12.3% | 2.0% |
| CD34$^-$/CD38$^-$ | 12.9% | 17.4% | 54.1% |
| CD34$^-$/CD38$^+$ | 72.2% | 60.4% | 26.4% |

As a result, the CD34$^+$ cell proliferation potential was lower for rHSA than for plasma-derived HSA (Table 13). However, the CFU-GM, BFU-E, and CFU-Mix expansion potentials were higher for rHSA than for plasma-derived HSA (Tables 14 and 15). The CD34$^+$/CD38$^-$ cell expansion potential was higher for rHSA than for plasma-derived HSA (Table 16).

From these results, it was demonstrated that rHSA is superior to plasma-derived HSA in terms of the expansion of CFU-GM, BFU-E, and CFU-Mix, and that it is superior to plasma-derived HSA in terms of the expansion of CD34$^+$/CD38$^-$ cells.

Experimental Example 7

Comparison of Potency Between Serum Medium and Serum-Free Medium

Potency was compared between a serum medium (FCS) and a serum-free medium based on rh-HSA stock solution.

The method of cultivation, medium composition, method of surface antigen analysis, and colony assay method used were the same as those in Experimental Example 1.

The medium supplemented with stock solution rh-HSA was prepared by adding a 2% rh-HSA stock solution (Mitsubishi Pharma Corporation), 200 µg/ml transferrin, 100 µg/ml cholesterol, 160 µg/ml lecithin, 1 µg/ml insulin, 1 µg/ml tocopherol, and 1 µg/ml ascorbic acid to αMEM as the basal medium. At the time of cultivation, 100 ng/ml SCF, 10 ng/ml TPO, 100 ng/ml FL, 100 ng/ml IL6, and 100 ng/ml sIL6R were combined to prepare a complete serum-free medium.

7.1. Expansion of CD34-Positive Cells by Culture $2 \times 10^4$ of CD34-positive cells derived from umbilical cord blood were seeded to each of the serum medium and rh-HSA stock solution medium. Total cultured cell counts on day 12 of cultivation were measured, and the expansion rates were calculated. The results are shown in Table 17.

TABLE 17

|  | Proliferation rate |
|---|---|
| FCS | 402.7 |
| Recombinant HSA stock solution | 388 |

7.2. Comparison of Colony Formation Potentials

Cells on day 12 of cultivation (Table 18) were cultured for 2 weeks, and their colony formation potentials were compared. The expansion rate of total colony forming cells was 97.5 fold for the serum culture and 161.1 fold for the recombinant HSA stock solution. The expansion rate of CFU-MIX colony forming cells, which reflects the potential of more blastogenic hematopoietic stem cells, was 57.6 fold for the serum culture and 111 fold for the recombinant HSA stock solution.

TABLE 18

|  | CD34$^+$ cells | FCS | Recombinant HSA stock solution |
|---|---|---|---|
| CFU-GM | 5333 | 783858 | 1215733 |
| BFU-E | 2773 | 21476 | 108640 |
| CFU-Mix | 373 | 21476 | 41387 |
| Total count | 8480 | 826809 | 1365760 |

7.3. Expansion of CD34-Positive/CD38-Negative Cells

Analyzed using FACS. Cells on day 12 of cultivation were compared. The results are shown in Table 19. The CD34-positive/CD38-negative fraction is considered to be the most undifferentiated hematopoietic stem cell fraction.

TABLE 19

|  | FCS | Recombinant HSA stock solution |
|---|---|---|
| CD34-positive/CD38-negative | 10.43 | 41.95 |
| CD34-positive/CD38-positive | 23.73 | 8.31 |
| CD34-negative/CD38-negative | 14.48 | 26.95 |
| CD34-negative/CD38-positive | 51.36 | 22.78 |

7.4. Expansion of CD34-Positive/CD38-Negative/HLA-DR-Negative Cells

Since not only the CD34-positive/CD38-negative fraction but also the HLA-DR-negative fraction is blastogenic, analysis was performed using FACS and a comparison was made on day 12 of cultivation. The results are shown in Table 20. The expansion rate was 7.35% for the serum culture and 15.15% for the recombinant HSA stock solution.

TABLE 20

|  | FCS | Recombinant HSA stock solution |
|---|---|---|
| CD34-positive/CD38-positive/HLA-DR-negative | 18.44 | 2.5 |
| CD34-positive/CD38-positive/HLA-DR-positive | 52.99 | 15.47 |
| CD34-positive/CD38-negative/HLA-DR-negative | 7.35 | 15.15 |
| CD34-positive/CD38-negative/HLA-DR-positive | 21.22 | 66.88 |

7.5. Ratio of Differentiated Blood Cells (Blood Cell Lineage Analysis Using Various Monoclonal Antibodies and FACS)

With CD3 (T lymphocytes), CD19 (B lymphocytes), glycophorin A (erythroblasts and erythrocytes), CD41 (megakaryocytes and platelets), CD14 (monocytes), CD33 (blastogenic granulocytes and monocytes), and CD66b (mature granulocytes) as indices of degree of blood cell differentiation, surface antigens of cultured cells were analyzed and compared (Table 21).

TABLE 21

|   | FCS | Recombinant HSA stock solution |
|---|---|---|
| CD3 | 0.11 | 0.07 |
| Glycophorin A | 0.36 | 0.14 |
| CD19 | 0 | 0 |
| CD41 | 0.57 | 6.02 |
| CD14 | 19.74 | 12.56 |
| CD33 | 93.09 | 88.6 |
| CD66b | 6.24 | 2.18 |

The morphological classification of cultured cells by Giemsa staining is summarized in Table 22. Although the ratio of differentiated mature cells increased during 12 days of serum culture, blasts accounted for not less than 40% with the recombinant HSA stock solution, suggesting that immaturity may tend to be maintained in the latter case.

TABLE 22

|   | FCS | Recombinant HSA stock solution |
|---|---|---|
| Blasts | 26 | 40 |
| Mature cells | 74 | 60 |

No major difference was observed between the expansion in the recombinant HSA stock solution medium and the expansion in the serum medium (Table 17).

Colony formation potential was greater for all analytical items, including total colony forming cell count, in the HSA stock solution medium than in the serum medium (Table 18).

In the analysis using FACS, both the CD34-positive/CD38-negative cells and CD34-positive/CD38-negative/HLA-DR-negative cells maintained a more blastogenic fraction in the HSA stock solution medium than in the serum medium (Tables 19 and 20).

Regarding the differentiation of cultured cells, it was found that the differentiation into the monocytic lineage and granulocytic lineage progressed more in the serum medium than in the HSA medium, and the differentiation into the megakaryocytic lineage progressed more in the HSA stock solution medium than in the serum medium (Table 21).

In the morphological classification by Giemsa staining, more blasts were observed in the order of HSA stock solution medium>FCS (Table 22).

From the results above, it was found that the HSA stock solution medium enhanced expansion while maintaining the proliferation potential of blastogenic cells.

Experimental Example 8

Evaluation of Hematopoietic Regeneration Potential

Using hematopoietic stem cells expanded using a serum-free medium containing recombinant HSA in Experimental Example 1, hematopoietic regeneration potential was evaluated in NOD mice. As a result, better results were obtained compared to hematopoietic stem cells derived from umbilical cord blood that had not undergone the expansion procedure.

INDUSTRIAL APPLICABILITY

The present invention is expected to find applications to regeneration medicine and cell transplantation because it provides various means enabling the expansion of undifferentiated hematopoietic cells in a more undifferentiated state. The present invention is also expected to find applications to regeneration medicine and cell transplantation because it enables the expansion of hematopoietic cells in a serum-free medium and avoids contamination with viruses and prion derived from serum components.

This application is based on a patent application No. 2004-13291 filed in Japan on Jan. 21, 2004, the contents of which are incorporated in full herein by this reference.

The invention claimed is:

1. A method of expanding a hematopoietic stem cell, which comprises
   (i) forming a first solution comprising cholesterol,
   (ii) adding the first solution to a serum-free medium to form a second solution, wherein the second solution further comprises lecithin, tocopherol, stem cell factor, thrombopoietin, Flt3/Flk2 ligand, interleukin-6, soluble interleukin-6 receptor, and a recombinant human serum albumin (rHSA)-containing composition obtained from yeast, and
   (iii) culturing a hematopoietic stem cell in the second solution to expand the hematopoietic stem cell and to suppress differentiation of the hematopoietic stem cell.

2. The method of claim 1, which further comprises isolating the hematopoietic stem cell.

3. The method of claim 2, wherein the hematopoietic stem cell is derived from umbilical cord blood.

4. The method of claim 2, wherein the expanded hematopoietic stem cell is selected from the group consisting of $CD34^+/CD38^-$, $CD34^+/DR^-$, $CD34^+/CD90^+$, $CD34^+/CD117^+$, $CD34^+/CD123^+$, and $CD34^+/CD133^+$.

5. The method of claim 2, wherein the expanded hematopoietic stem cell is $CD34^{+/CD}38^-/DR^-$.

6. The method of claim 2, wherein the first solution further comprises ethanol.

7. The method of claim 2, wherein the expanded hematopoietic stem cell is $CD34^+/CD38^-$.

8. The method of claim 1, wherein the hematopoietic stem cell is derived from umbilical cord blood.

9. The method of claim 1, wherein the expanded hematopoietic stem cell is $CD34^+/CD38^-/DR^-$.

10. The method of claim 1, wherein the serum-free medium comprises a basal medium.

11. The method of claim 10, which further comprises administering the hematopoietic stem cell to a patient.

12. The method of claim 11, wherein the patient is undergoing cell transplant therapy.

13. The method of claim 11, wherein the hematopoietic stem cell is derived from umbilical cord blood.

14. The method of claim 11, wherein the expanded hematopoietic stem cell is selected from the group consisting of $CD34^+/CD38^-$, $CD34^+/DR^-$, $CD34^+/CD90^+$, $CD34^+/CD117^+$, $CD34^+/CD123^+$, and $CD34^+/CD133^+$.

15. The method of claim 11, wherein the expanded hematopoietic stem cell is $CD34^+/CD38^-/DR^-$.

16. The method of claim 11, wherein the first solution further comprises ethanol.

17. The method of claim 11, wherein the expanded hematopoietic stem cell is CD34+/CD38−.

18. The method of claim 1, wherein the first solution further comprises ethanol.

19. The method of claim 1, wherein the expanded hematopoietic stem cell is $CD34^+/CD38^-$.

20. A method of expanding a hematopoietic stem cell, which comprises
   (i) forming a first solution comprising cholesterol,
   (ii) adding the first solution to a serum-free medium to form a second solution, wherein the second solution further comprises lecithin, tocopherol, stem cell factor, thrombopoietin, Flt3/Flk2 ligand, interleukin-6, soluble interleukin-6 receptor, and a recombinant human serum albumin (rHSA)-containing composition obtained from yeast, and
   (iii) culturing a hematopoietic stem cell in the second solution to expand the hematopoietic stem cell and to suppress differentiation of the hematopoietic stem cell, wherein the expanded hematopoietic stem cell is selected from the group consisting of $CD34^+/CD38^-$, $CD34^+/DR^-$, $CD34^+/CD90^+$, $CD34^+/CD117^+$, $CD34^+/CD123^+$, and $CD34^+/CD133^+$.

* * * * *

UNITED STATES PATENT AND TRADEMARK OFFICE
CERTIFICATE OF CORRECTION

PATENT NO.         : 8,168,429 B2                                        Page 1 of 1
APPLICATION NO.    : 10/587014
DATED              : May 1, 2012
INVENTOR(S)        : Hatsuyama et al.

It is certified that error appears in the above-identified patent and that said Letters Patent is hereby corrected as shown below:

In the Claims

Claim 5, Column 22, Line 39, "$CD34^{+/CD}38^-/DR^-$" should read "$CD34^+/CD38^-/DR^-$"

Claim 17, Column 22, Line 65, "CD34+/CD38-" should read "$CD34^+/CD38^-$"

Signed and Sealed this
Sixth Day of November, 2012

David J. Kappos
*Director of the United States Patent and Trademark Office*